United States Patent [19]

Segal

[11] 4,313,434
[45] Feb. 2, 1982

[54] FRACTURE FIXATION

[76] Inventor: David Segal, 229 Fuller St., West Newton, Mass. 02165

[21] Appl. No.: 197,794

[22] Filed: Oct. 17, 1980

[51] Int. Cl.³ .......................... A61B 17/18; A61F 5/04
[52] U.S. Cl. .............................. 128/92 BC; 128/92 G; 128/DIG. 20
[58] Field of Search .............. 128/92 BC, 92 R, 92 G, 128/87, 89, 90, DIG. 20

[56] References Cited

U.S. PATENT DOCUMENTS

| 3,091,237 | 5/1963 | Skinner | 128/DIG. 20 |
| 3,332,415 | 7/1967 | Ericson | 128/87 R |
| 3,710,789 | 1/1973 | Ersek | 128/92 BC |
| 3,760,802 | 9/1973 | Fischer et al. | 128/92 BC |
| 3,954,102 | 5/1976 | Buuck | 128/DIG. 20 |

FOREIGN PATENT DOCUMENTS 662082 5/1979 U.S.S.R. .......................... 128/92 BC

Primary Examiner—Ronald L. Frinks
Attorney, Agent, or Firm—Charles Hieken

[57] ABSTRACT

Fixation of a long bone is accomplished by drilling a small opening into the medullary cavity, inserting a deflated flexible bladder into the medullary cavity through the opening, inflating the bladder with sterile air through an opening accessible outside the bone, sealing the opening, unsealing the opening after the fracture has healed, removing the bladder and then filling the opening.

11 Claims, 3 Drawing Figures

FRACTURE FIXATION

The present invention relates in general to fracture fixation and more particularly concerns novel intramedullary devices and techniques for fracture fixation using inflatable flexible materials that are relatively easy to install while reducing surgical exposure, providing better fixation, enhancing healing, reducing intramedullary reaming and vascular damage and more closely matching the modulus of elasticity of the bone.

Prior art intramedullary devices typically comprise a thick rod or multiplicity of thin rods in various shapes and designs for fixation of long bones of the body. The long bones, such as the thigh bone, the lower leg bone and the bones of the arm and forearm are tubular with a cavity (called the medullary cavity). When a long bone has been fractured, metal rods inserted into the medullary cavity hold the broken ends together until healing takes place. The thigh bone (femur) is the long bone most often treated surgically in this manner. However, in order to get adequate stability, the cavity must be filled tightly with the intramedullary rod. This condition requires an extensive procedure which involves reaming the medullary cavity (thus destroying the inner lining of blood vessels) for inserting a bigger rod. A bigger and tighter rod inside the medullary cavity enhances the stability of the fragments. Meeting this condition requires a bigger hole in the bone for rod insertion.

The ends of long bones in children are also the growth centers of the bones. Drilling through causes damage and stops or deforms further growth. For that reason no rod can be inserted into a broken bone of a growing child.

It is an important object of this invention to provide improved devices and techniques for fracture fixation.

It is another object of the invention to achieve the preceding object while reducing surgical exposure.

It is a further object of the invention to achieve one or more of the preceding objects while attaining better fixation.

It is still another object of the invention to achieve one or more of the preceding objects while enhancing healing.

It is still another object of the invention to achieve one or more of the preceding objects while fighting infection.

Still another object of the invention is to achieve one or more of the preceding objects with reduced stiffness.

It is still another object of the invention to achieve one or more of the preceding objects with apparatus that is relatively inexpensive and relatively easy to install.

According to the invention, a small opening is made from outside the fractured long bone into the medullary cavity, a hollow flexible deflated bladder is inserted through the opening into the medullary cavity along the length of the bone extending on opposite sides of the fracture, and the bladder is inflated through an opening outside the long bone until the bladder engages the walls of the medullary cavity to firmly support the fractures bone. The opening can be made at any part of the broken bone and an appropriate shaped inflatable device introduced. With a bladder insertion can be without entering either end or growth zone (epiphysis). When the fracture has healed, the bladder may be deflated and removed, and the opening filled. The outside of the bladder may be coated with antibiotics or ions to enhance healing or fight infection. The bladder may take a form to provide better fixation after inflating; for example, by being narrower in the middle than at both ends to better conform to the shape of the medullary canal. The bladder may be made of rubber or suitable flexible plastic materials, such as polyethylene. Inflation may be with sterile air, oxygen, nitrogen, other suitable gas or sterile fluid. The opening is preferably near one end of the medullary cavity; however, it need not be along the cavity axis, but could be at an angle to it to facilitate drilling while minimizing the surgical exposure.

Numerous other features, objects and advantages of the invention will become apparent from the following specification when read in connection with the accompanying drawing in which.

Figure 1:
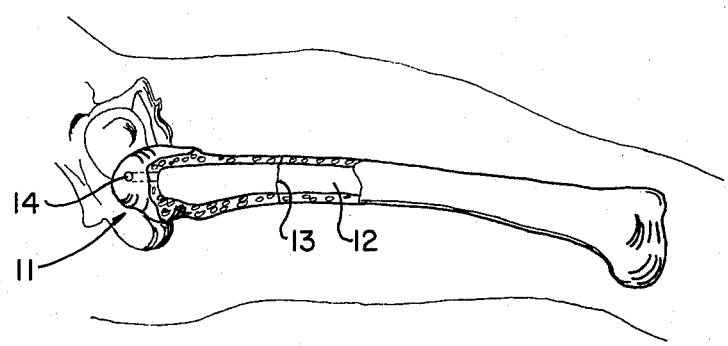
FIG. 1 is a sectional view of a portion of a fractured long bone showing an opening drilled along the axis according to the invention for admitting the bladder.

With reference now to the drawing and more particularly FIG. 1 thereof, there is shown a sectional view of a portion of a long bone, such as a thigh bone, lower leg bone, and bones of the arm and forearm that are tubular with a medullary cavity 12 having a fracture 13. FIG. 1 shows the fractured bone 11 reset and with an opening 14 having been drilled by the orthopedic surgeon for receiving a flexible hollow bladder.

Figure 2:
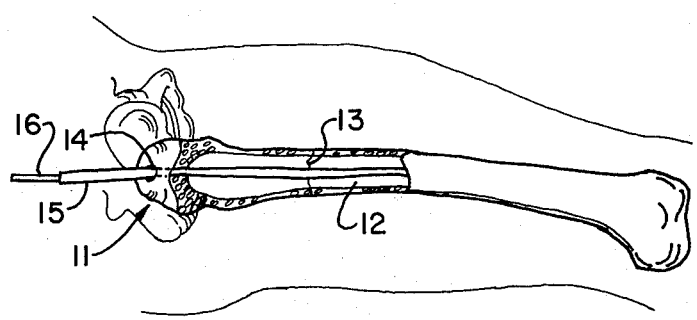
FIG. 2 is a sectional view of the bone portion of FIG. 1 showing the deflated bladder entering the cavity.
Figure 3:
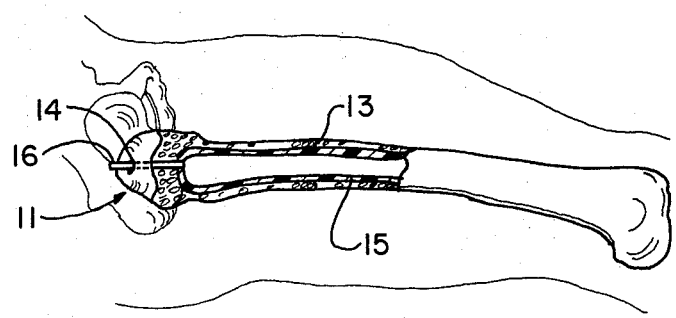
FIG. 3 is a sectional view of the long bone portion of FIGS. 1 and 2 showing the bladder inflated in the medullary cavity providing fixation according to the invention.

With reference to FIG. 2, there is shown the sectional view of the portion of long bone 11 shown in FIG. 1 with deflated bladder 15 entering through opening 14. When bladder 15 has entered the medullary cavity 12 to a point where opening 16 is just outside bone 11, bladder 15 is then inflated until it firmly engages the walls of medullary cavity 12 as shown in FIG. 3 with bladder 15 shown partially in section. The opening 16 of bladder 15 is then sealed to maintain bladder 15 inflated to provide fixation. The sealing may be effected by heat sealing, plugging, a valve for repeated inflations useful in distraction or other suitable means. When the fractured long bone has healed, opening 16 may be unsealed, bladder 15 deflated and removed. Opening 14 may then be filled, or alternatively, allowed to grow closed.

The bladder may be made of natural or synthetic rubberlike materials, polyethylene or other suitable flexible materials capable of remaining inflated. The inflating medium may be sterile air, oxygen, nitrogen, other suitable gases, or other fluids, such as sterile water. The outside of the bladder may be coated with antibiotics or ions to enhance healing or fight infection.

The invention has a number of advantages. It significantly reduces surgical exposure because the bladder may be inserted through a smaller hole into the bone than metal rods, reaming is not required and entry may be made through a more accessible opening clear of growth regions in growing children. The bladder may be shaped to provide better fixation after inflation; for example, shaped to conform to the shape of the medullary canal by being thinner in the middle than at each end. It may enhance healing or fighting infection by being coated with antibiotics and/or ions. The modulus of elasticity of the inflated bladder is believed to be more nearly equal to that of the surrounding bone than metal rods, thereby reducing the bad effects of a rod that is too stiff or rigid. Removal of the bladder after healing is accomplished with less surgical exposure than removing a metal rod.

The outer surface of the bladder may be smooth or serrated for a better grip.

There has been described novel apparatus and technique for fixation of long bones of the body. It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. A method of long bone fixation which method includes the steps of, forming an opening in a long bone extending from the outside of the bone into the medullary cavity, inserting a deflated flexible bladder through said opening into said medullary cavity, and then inflating said bladder until the inflated bladder firmly engages the walls of said medullary cavity to provide fixation of said long bone.

2. A method of long bone fixation in accordance with claim 1 wherein said bladder is inflated through an opening accessible from outside said bone and further including the step of sealing said opening after said bladder has been inflated.

3. A method in accordance with claim 2 and further including the step of unsealing said opening after said long bone has healed to deflate said bladder.

4. A method in accordance with claim 3 and further including the step of removing said bladder.

5. A method in accordance with claim 4 and further including the step of filling said opening.

6. A long bone fixation made in accordance with the method of claim 2 with said inflated bladder firmly engaging the walls of said medullary cavity.

7. A long bone fixation in accordance with claim 6 wherein said bladder is made of material from the group consisting of natural rubber-like material, synthetic rubber-like material and flexible plastic.

8. A long bone fixation in accordance with claim 6 and further comprising fluid means inside said bladder for maintaining said bladder in firm engagement with the walls of said medullary cavity.

9. A long bone fixation in accordance with claim 8 wherein said fluid means is from the group consisting of sterile air, sterile oxygen, sterile nitrogen, sterile gas and liquid.

10. A long bone fixation in accordance with claim 6 wherein said bladder is formed with an inflated shape that is narrower in the middle than at each end for improved conformity with the shape of said medullary cavity.

11. A long bone fixation in accordance with claim 6 wherein the outer surface of said inflated bladder is serrated.

* * * * *